(12) United States Patent
Ridler et al.

(10) Patent No.: US 10,118,043 B2
(45) Date of Patent: Nov. 6, 2018

(54) COIL FOR SIGNAL TRANSMISSION TO IMPLANTABLE DEVICE

(71) Applicant: COCHLEAR LIMITED, Macquarie University (AU)

(72) Inventors: Oliver John Ridler, Macquarie University (AU); Adam Mujaj, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 0 days.

(21) Appl. No.: 14/542,286

(22) Filed: Nov. 14, 2014

(65) Prior Publication Data

US 2015/0265842 A1 Sep. 24, 2015

Related U.S. Application Data

(60) Provisional application No. 61/954,921, filed on Mar. 18, 2014.

(51) Int. Cl.
*A61N 1/378* (2006.01)
*A61N 1/372* (2006.01)
*A61N 1/36* (2006.01)

(52) U.S. Cl.
CPC ..... *A61N 1/37229* (2013.01); *A61N 1/36036* (2017.08)

(58) Field of Classification Search
CPC .................................................. A61N 1/37229
See application file for complete search history.

(56) References Cited

U.S. PATENT DOCUMENTS

| | | | |
|---|---|---|---|
| 5,314,453 A | 5/1994 | Jeutter | |
| 5,991,664 A * | 11/1999 | Seligman | A61N 1/3787 607/55 |
| 8,280,524 B2 | 10/2012 | Duftner et al. | |
| 2008/0002834 A1 | 1/2008 | Hochmair | |
| 2008/0027500 A1 | 1/2008 | Chen | |
| 2008/0082147 A1* | 4/2008 | Dai | A61N 1/3787 607/61 |
| 2011/0224789 A1 | 9/2011 | Griffith | |
| 2012/0119700 A1* | 5/2012 | Forsell | A61N 1/37229 320/108 |
| 2013/0066398 A1 | 3/2013 | Duftner et al. | |

* cited by examiner

*Primary Examiner* — George Evanisko
(74) *Attorney, Agent, or Firm* — Merhcant & Gould P.C.

(57) ABSTRACT

A cochlear implant or other auditory prosthesis utilizes an external portion worn on a recipient's head and an internal portion implanted therein. Both portions include an associated coil that transmits a signal between the two portions. The external coil has a form factor substantially similar to the implantable coil. This form factor allows the external portion to be manufactured with a smaller footprint, since components that may otherwise interfere with signal transmission (e.g., batteries) may be installed closer to the external coil.

21 Claims, 10 Drawing Sheets

FIG.9

COIL FOR SIGNAL TRANSMISSION TO IMPLANTABLE DEVICE

CROSS-REFERENCE TO RELATED APPLICATIONS

This application claims priority to and the benefit of U.S. Provisional Patent Application No. 61/954,921, filed Mar. 18, 2014, entitled "COIL FOR SIGNAL TRANSMISSION TO IMPLANTABLE DEVICE," the disclosure of which is incorporated by reference herein in its entirety.

BACKGROUND

Auditory prostheses, such as cochlear implants, include an implantable portion having a stimulating assembly with an implanted coil and an external portion having a coil, speech processing hardware and software, as well as a battery. Recipients of such devices desire the external portion to be as light and small as possible, both for comfort and unobtrusiveness. Reducing the size of such external portions is complicated however, since positioning the various components, e.g., the batteries and coil, closer to each other can reduce the quality of signals sent between the external and implanted coils.

SUMMARY

Embodiments disclosed herein relate to systems and apparatuses that are used to transmit data between external and internal portions of medical devices. Those devices include, for example, cochlear implants or other auditory prostheses or devices. The external portion of the auditory prosthesis is powered by an on-board battery and sends signals via a coil. An implanted coil receives the signals and provides stimulation to the device recipient. The form factor of the external coil allows the external portion of the device to be small and discreet, while still providing high quality data transmission to the implantable coil.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
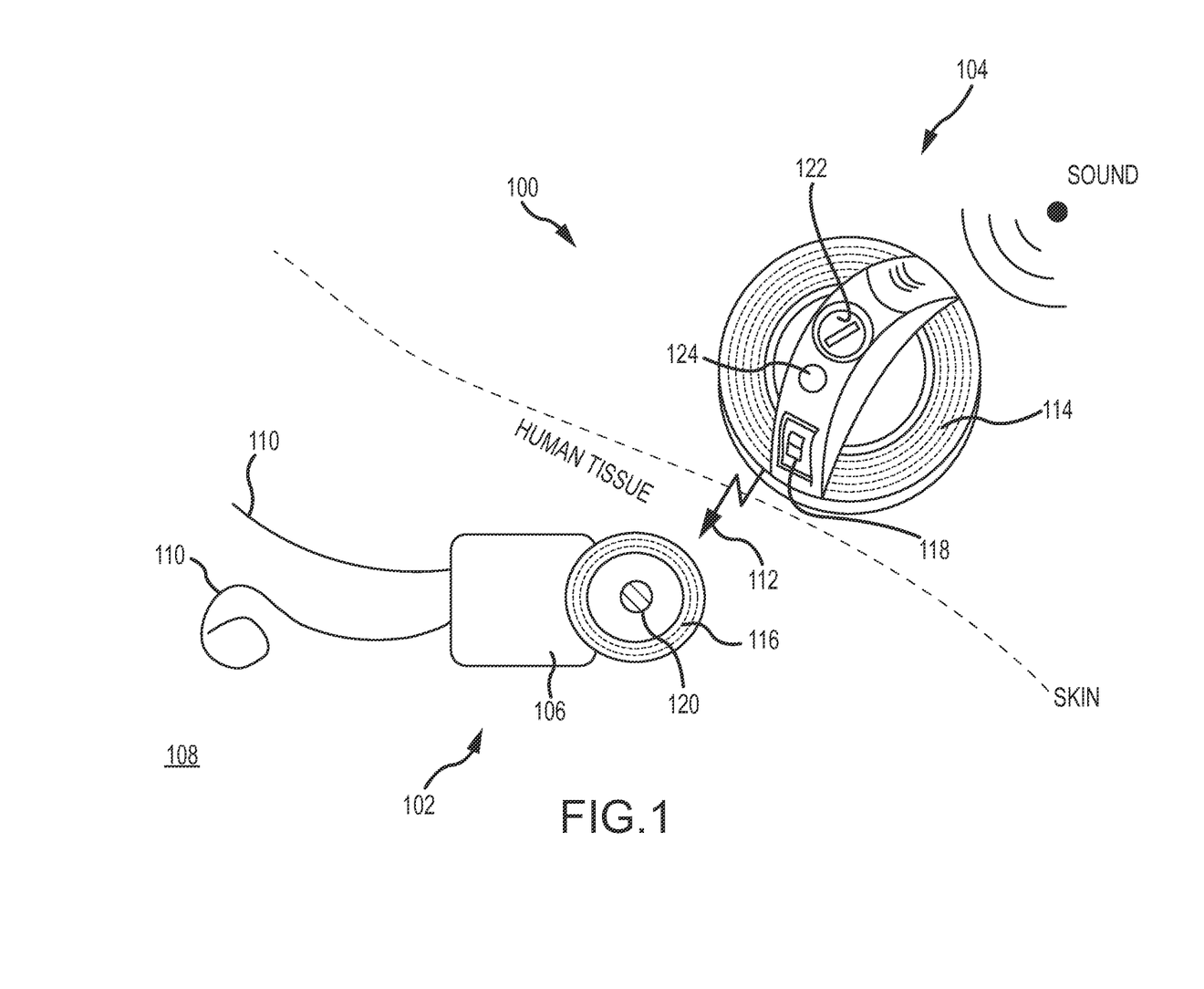
FIG. 1 is a perspective view of an auditory prosthesis, including an implantable portion and an external portion.

While the technologies disclosed herein have particular application in the cochlear implant devices depicted in FIG. 1, it will be appreciated that the systems, methods, and apparatuses disclosed can be employed in other types of hearing prostheses. For example, the embodiments disclosed herein can be used to power active transcutaneous bone conduction devices, passive transcutaneous devices, or other devices that include an external coil and an internal or implantable coil. Furthermore, the embodiments disclosed herein can be utilized to transmit signals to medical devices other than hearing prostheses. The technologies disclosed herein will be described generally in the context of external portions of medical devices where the external portions utilize a coil for transmission of data or other signals. Such signals can also include signals sent by a charging coil that charges a totally-implantable cochlear implant or other medical device. For clarity, however, the technology will be described in the context of cochlear implant auditory prostheses and, more specifically, the external portions and coils used therewith.

FIG. 1 is a perspective view of an auditory prosthesis 100, in this case, a cochlear implant, including an implantable portion 102 and an external portion 104. The implantable portion 102 of the cochlear implant includes a stimulating assembly 106 implanted in a body (specifically, proximate and within the cochlea 108) to deliver electrical stimulation signals to the auditory nerve cells, thereby bypassing absent or defective hair cells. The electrodes 110 of the stimulating assembly 106 differentially activate auditory neurons that normally encode differential pitches of sound. This stimulating assembly 106 enables the brain to perceive a hearing sensation resembling the natural hearing sensation normally delivered to the auditory nerve.

The external portion 104 includes a speech processor that detects external sound and converts the detected sound into a coded signal 112 through a suitable speech processing strategy. The coded signal 112 is sent to the implanted stimulating assembly 106 via a transcutaneous link. The signal 112 is sent from an external coil 114 located on the external portion 104 to an implantable coil 116 on the implantable portion 102, via a radio frequency (RF) link. The signal 112 can be data, power, audio, or other types of signals, or combinations thereof. These coils 114, 116 are typically both circular in shape to maximize the coupling of magnetic flux. The efficiency of power transfer and integrity of the data transmission from one coil to the other is affected by the coil coupling coefficient (k). Coil coupling coefficient k is a unitless value that indicates the amount of the shared magnetic flux between a first coil and a second, coupled (associated) coil. As the amount of shared magnetic flux decreases (i.e., as the coil coupling coefficient k decreases), efficient power transfer between the two coils becomes increasingly difficult. Therefore it is advantageous to maximize the coil coupling coefficient k in a system where power and/or data are transferred between two coils. The stimulating assembly 106 processes the coded signal 112 to generate a series of stimulation sequences which are then applied directly to the auditory nerve via the electrodes 110 positioned within the cochlea 108. The external portion 104 also includes a battery and a status indicator 118. Permanent magnets 120, 122 are located on the implantable portion 102 and the external portion 104, respectively. In the depicted device, the external portion includes a microphone port 124 connected to a microphone that receives sound. The microphone is connected to one or more internal processors that process and convert the sound into stimulation signals that are sent to the implantable portion 102.

Figure 2:
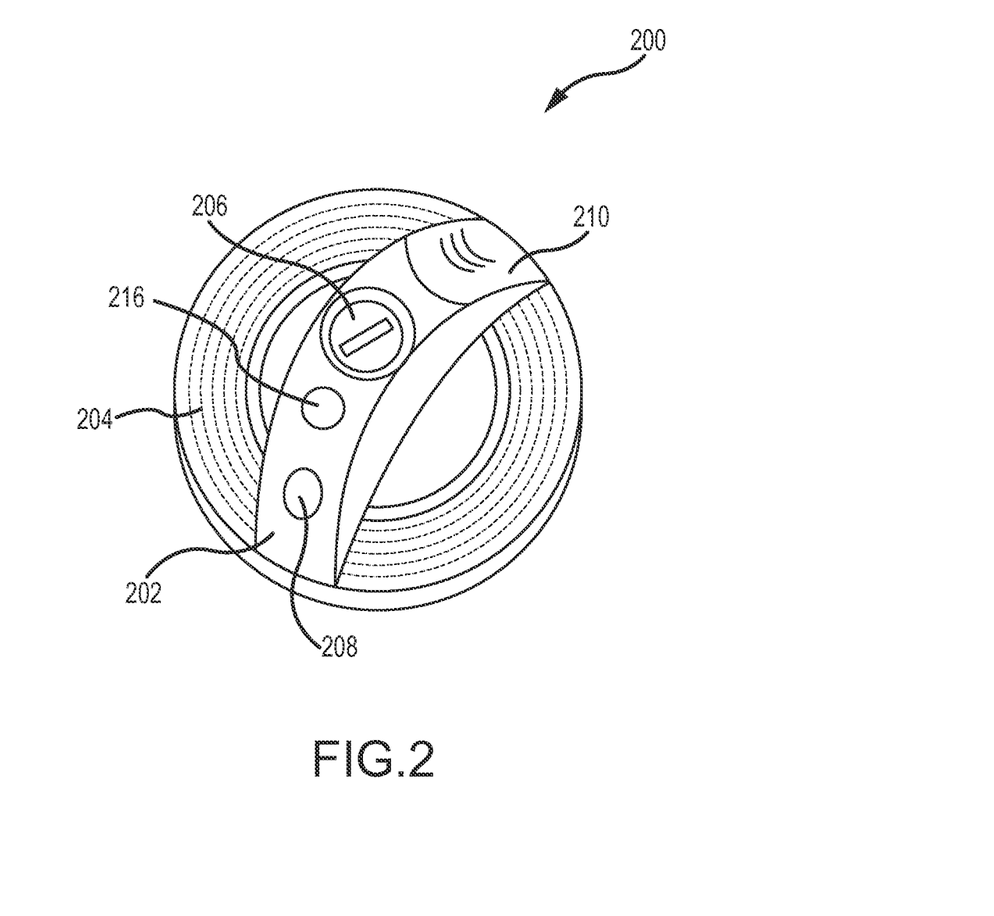
FIGS. 2-3 are perspective views of an external portion of an auditory prosthesis.
Figure 3:
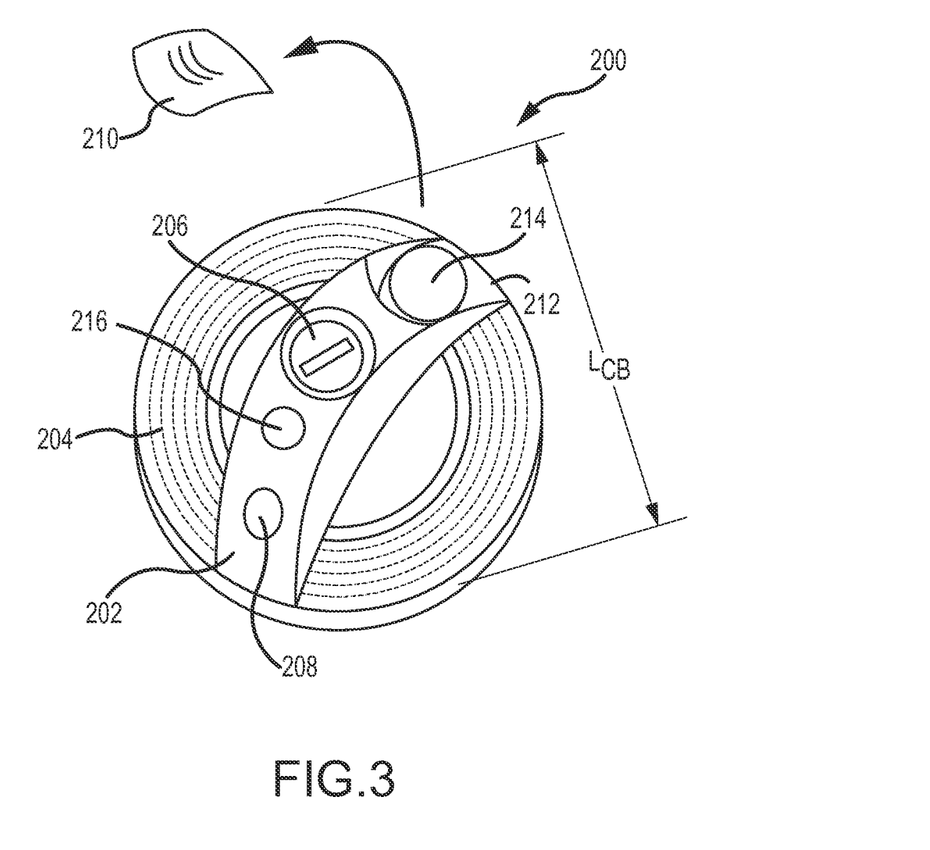

FIGS. 2-3 are perspective views of an external portion 200 of an auditory prosthesis and are described simultaneously. The external portion 200 includes a body 202 and an external coil 204 connected thereto. The body 202 can include a permanent magnet 206 as described above. The external portion 200 can include an indicator 208 such as a light emitting diode (LED). A battery door 210 (depicted removed in FIG. 3) covers a receptacle 212 that includes a battery 214 that provides internal power to the various components of the external portion 200 and the implantable portion. The battery 214 is matingly received in the receptacle 212. A microphone 216 receives sound that is processed by components within the external portion 200. As can be seen, the battery 214 is installed proximate the coil 204, generally above the coil 204 itself. It is desirable that auditory prostheses maintain a high coil quality factor (Q). Coil quality factor Q is a unitless value that indicates the how much energy is lost relative to the energy stored in the resonant circuit that includes the coil. A higher coil quality factor Q indicates a lower rate of energy loss relative to the stored energy of the resonant circuit. Coil quality factor Q can be calculated for an ideal series RLC circuit as depicted in Equation I:

$$Q = \frac{1}{R}\sqrt{\frac{L}{C}} = \frac{\omega_0 L}{R}$$

Here, L is the measured inductance of the coil, R is the measured resistance of the coil, and $\omega_0 = 2 \times Pi \times Frequency$. As the coil quality factor Q decreases, it becomes increasingly difficult to transfer power efficiently from one coil to an associated coil. Therefore, it is advantageous to maximize the coil quality factor Q in a system where power is transferred between two coils.

A high coil quality factor Q is desirable, even while the electronics and batteries are in close proximity to the coil, as depicted in FIGS. 2 and 3. Placing metallic components, e.g., a battery 214, above the coil 204, as depicted in FIGS. 2 and 3, has an adverse effect on coil Q, but does keep to a minimum the effective length $L_{CB}$ of the coil/battery arrangement which is directly related to the size of the external portion 200. In FIG. 3, the effective length Lcb is limited to the outer diameter of the coil 204. A reduced coil Q, however, results in a lower efficiency RF link, which ultimately results in a shorter battery life. To address this in the configuration depicted in FIGS. 2 and 3, a shielding material such as ferrite may be disposed between the battery 214 and coil 204. This can help alleviate the adverse effect on coil Q, but adds weight and size to the device, which is also undesirable, since the external portion 200 is worn on the head of a recipient.

Figure 4A:
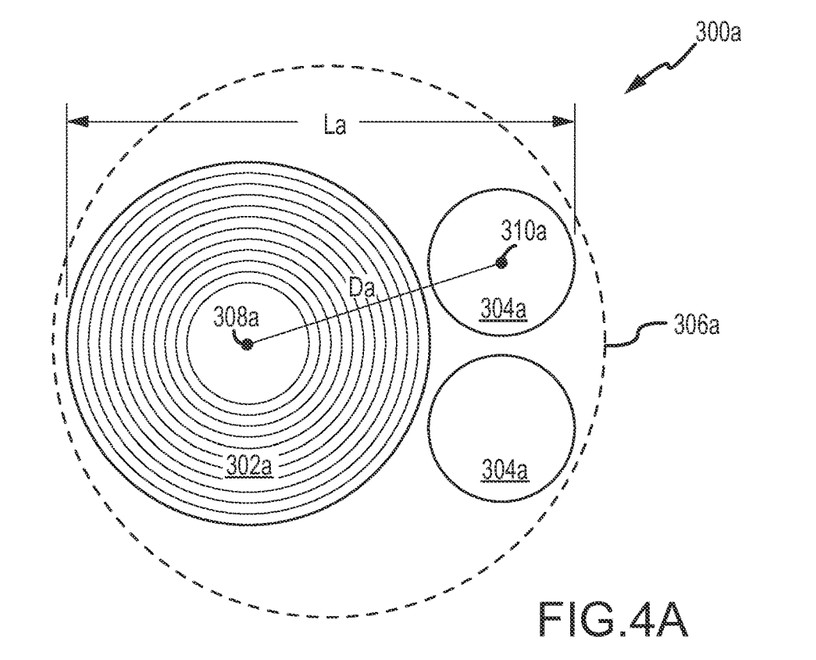
FIGS. 4A-4B depict schematic views of external portions of auditory prostheses.
Figure 4B:
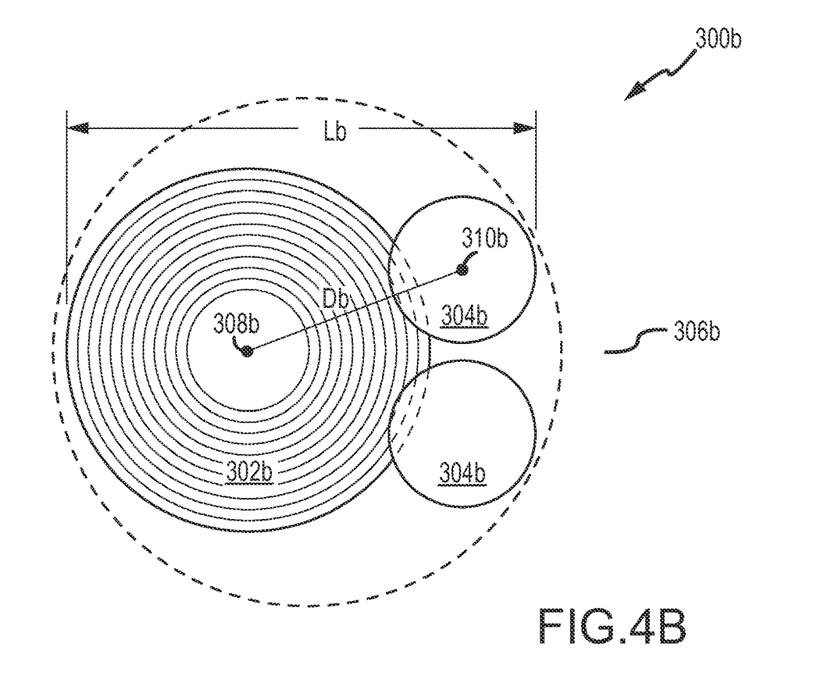

FIGS. 4A-4B depict schematic views of external portions 300 of auditory prostheses. In FIG. 4A, the external portion 300a includes an external coil 302a and, in this case, two batteries 304a. In contrast to the device of FIGS. 2 and 3, the external portion 300a of FIG. 4A is arranged such that the batteries 304a are disposed next to the coil 302a, where a center 308a of the coil 302a is a distance Da from a center 310a of the battery 304a. This configuration results in an increase in coil Q as compared to the device of FIGS. 2 and 3, but also a significant increase in the effective length La of the coil/battery arrangement. In testing, it has been discovered that the depicted arrangement has a coil Q of about 89.3 when the coil is made to resonate at about 5 MHz. Thus, in Equation I, L=5.288 µH, R=1.86 Ohms, and Frequency=5 MHz. This coil also has a coupling coefficient k to a second coil of about k=0.25 when the two coils are separated by about 3.0 mm. However, as apparent from FIG. 4A, this configuration ultimately increases the total footprint of a housing 306a of the external portion 300a, which is undesirable.

In FIG. 4B, the batteries 304b are arranged so as to only partially overlap the coil 302b, where a center 308b of the coil 302b is a distance Db from a center 310b of the battery 304b. Here, the distance Db is less than the distance Da of the device depicted in FIG. 4A. This shorter distance Db decreases the effective length Lb of the coil/battery arrangement (relative to the effective length La of FIG. 4A) and thus the housing 306b size. However, due to the proximity of the batteries 304b and the coil 302b, the drop in coil Q is significant and undesirable. In testing, it has been discovered that the depicted arrangement has a coil Q of about 36.4 when the coil is made to resonate at about 5 MHz. Thus, in Equation I, L=5.1 µH, R=4.4 Ohms, and Frequency=5 MHz. The coupling coefficient k is largely unchanged in this configuration because the size, shape, and relative position of the two coils has not changed.

Figure 5A:
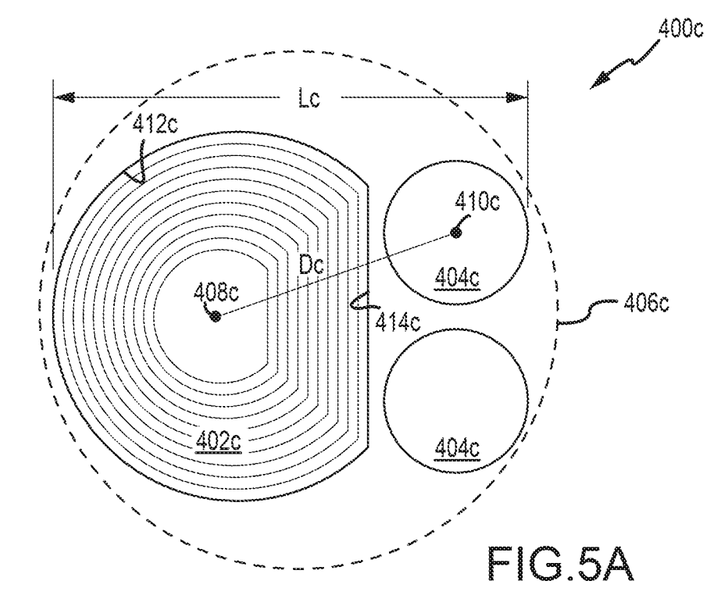
FIGS. 5A-5B depict schematic views of external portions of auditory prostheses in accordance with embodiments of the present disclosure.
Figure 5B:
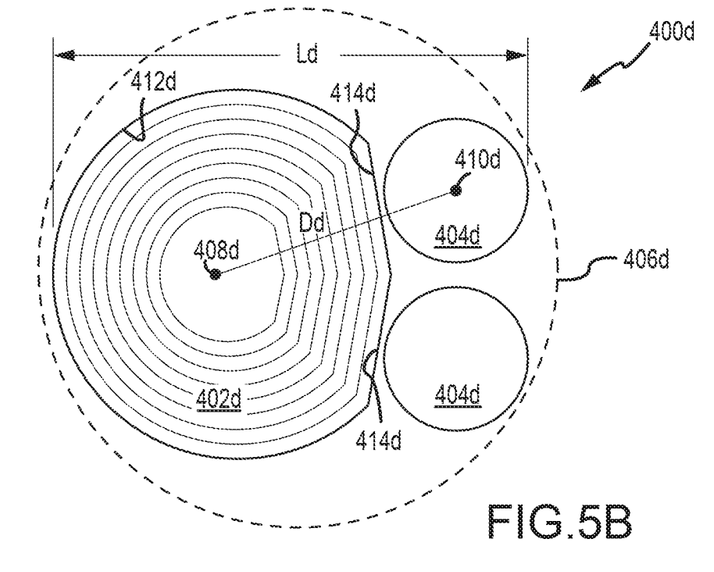

FIGS. 5A-5B depict schematic views of external portions 400c, 400d of auditory prostheses in accordance with embodiments of the present disclosure. In FIG. 5A, the external portion 400c includes an external coil 402c and two batteries 404c. The centers 408c, 410c, respectively, are a distance Dc from each other. Notably, this distance Dc is the same as the distance Db depicted in FIG. 4B, above. In this embodiment, however, the batteries 404c do not overlap the coil 402c. Instead, the outer perimeter of the coil 402c has been modified to decrease the total perimeter length as compared to the coils 302a, 302b depicted above, by including a curved (in this case, substantially circular) portion 412c and a substantially linear portion 414c. Coil 402c has a truncated circle shape. This modification from the round coils 302a, 302b depicted above enables the effective length Lc of the coil/battery arrangement to be substantially the same as the effective length Lb, which results in a similarly-sized housing 406c. It has been discovered that, by eliminating overlap between the coil 402c and batteries 404c, coil Q is substantially increased in comparison to the arrangement of FIG. 4B. In testing, the depicted embodiment of external device 400c has a coil Q of about 74.6 when the coil is made to resonate at about 5 MHz. Thus, in Equation I, L=5.268 µH, R=2.22 Ohms, and Frequency=5 MHz. This increase in coil Q is in excess of 200%, or double that the coil of FIG. 4B. A coil with the shape of 402c has a slightly smaller coupling coefficient k than a round coil. In testing, it has been discovered that the depicted arrangement has a coupling coefficient to a second coil of about k=0.24 when the two coils are separated by about 3.0 mm. By utilizing a truncated circular coil shape as depicted in FIG. 5A, instead of a round coil as depicted in FIG. 4B, coil quality factor Q has more than doubled, while but the coil coupling coefficient k has only reduced by about 4% (from about 0.25 to about 0.24). The resulting power transfer efficiency increase is a significant benefit of the coil shape 402c.

In FIG. 5B, the external portion 400d includes a coil 402d and two batteries 404d. The centers 408d, 410d, respectively, are a distance Dd from each other. Notably, this distance Dd is the same as the distance Db depicted in FIG. 4B, above. In this embodiment, the outer perimeter of the coil 402d also has been modified to decrease the total perimeter length, by including a curved (in this case, substantially circular) portion 412d and two substantially linear portions 414d. This modification enables the effective length Ld of the coil/battery arrangement to be substantially the same as the effective length Lb, which results in a similarly-sized housing 406d. It has been discovered that, by eliminating overlap between the coil 402d and batteries 404d, coil Q is substantially increased in comparison to the arrangement of FIG. 4B. Coil Q is anticipated to be similar to that of the prosthesis 400c. In the external portions 400c, 400d, a shielding material such as ferrite may be disposed between the batteries and coil to further increase Q, although, as described above, this may increase weight of the external portion 400c, 400d.

Figure 6A:
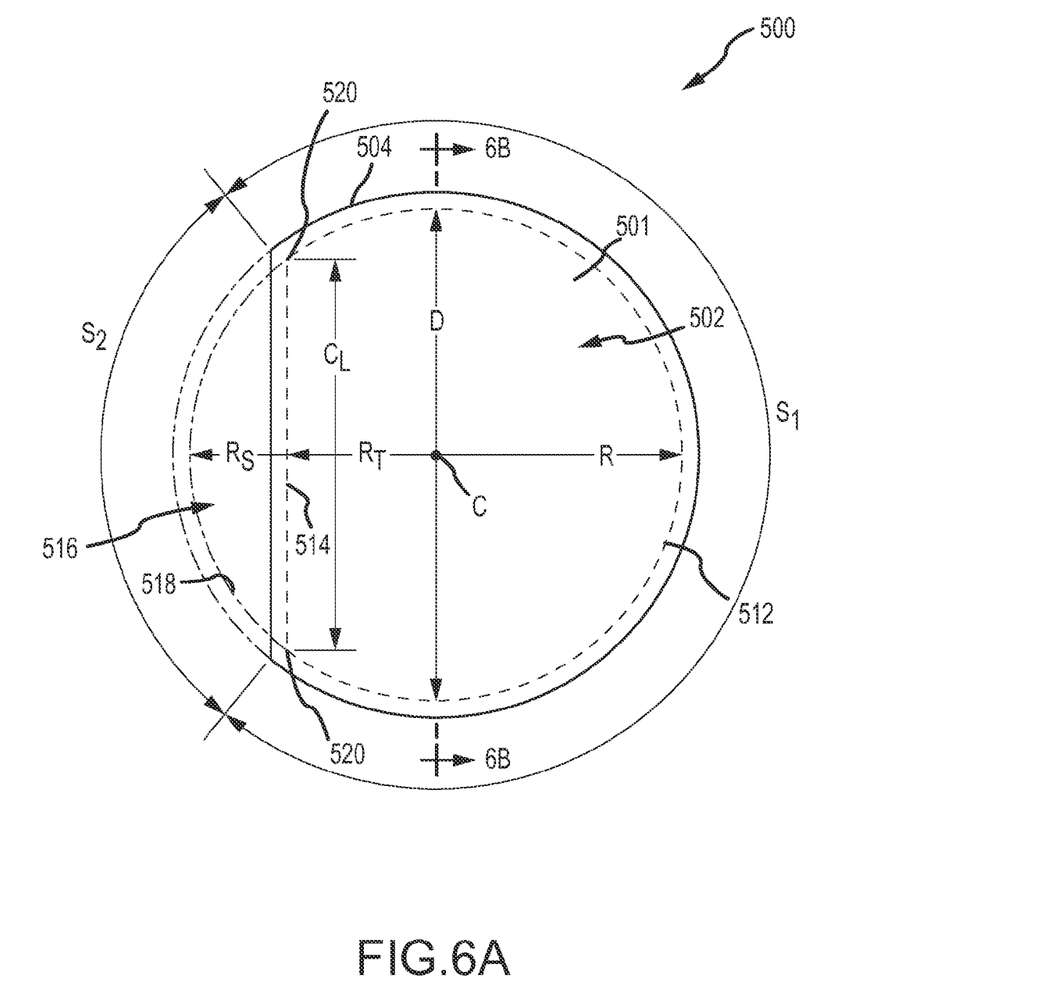
FIGS. 6A-6B depict a top view and a side sectional view, respectively, of a bobbin utilized in embodiments of the present disclosure.
Figure 6B:
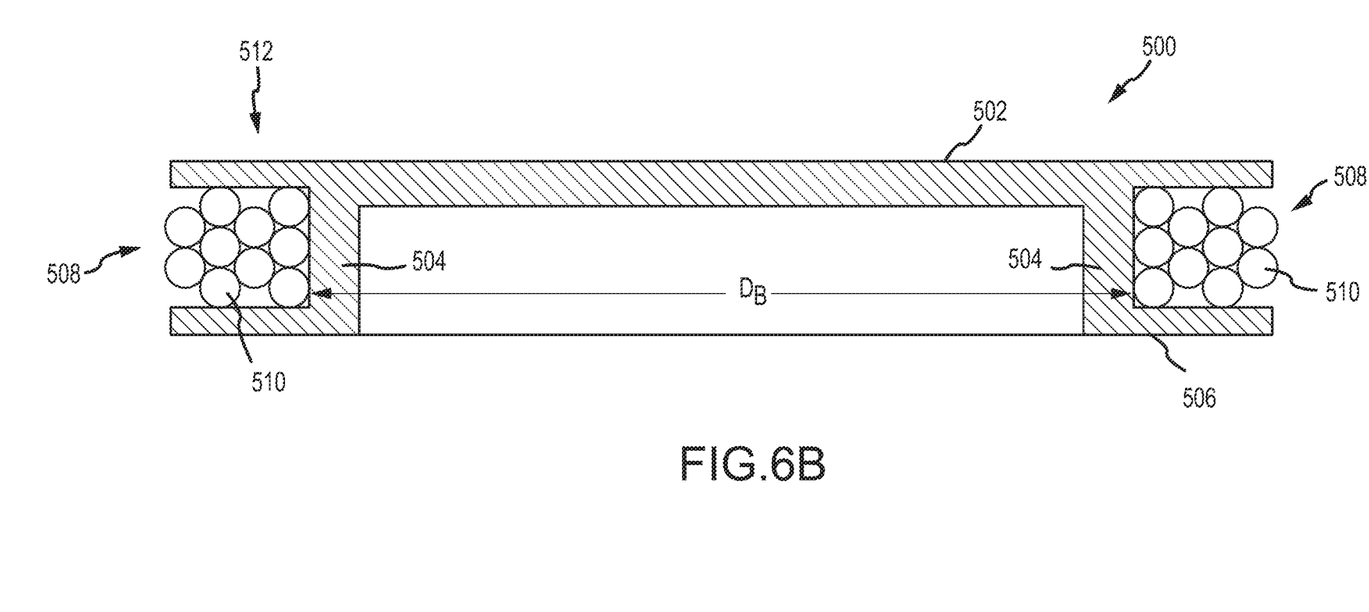

FIGS. 6A-6B depict a top view and a side sectional view, respectively, of a bobbin 500 utilized in embodiments of the present disclosure, and are described together. The bobbin 500 is used as a base about which to wind a wire 510 to form an external coil 512 to be utilized in an auditory prosthesis. The bobbin 500 includes a base plate 502 with a ring 504 extending therefrom. A second plate 506 is disposed parallel to the base plate 502 so as to form a channel 508 at least partially defined therebetween. The channel 508 is configured so as to receive the wire 510 that is wound about the ring 504, in a particular arrangement, so as to form the coil 512. In the depicted embodiment, the wire 510 is a 40 strand, 46 AWG wire having a diameter of about 420 μm, and is wound ten times to form the coil 512. Wires having other diameters or sizes can be utilized to form a coil, which can have greater than or fewer than ten turns.

In certain embodiments, the shape of the bobbin 500 and the coil 512 contained therein, can be defined by the geometric structure thereof. The depicted bobbin 500 (and therefore, the coil 512) has a shape of a truncated circle 501. In other embodiments, the bobbin can be a D-shape. In the depicted embodiment, the diameter D represents an interior diameter of the bobbin 500 and, therefore, the interior diameter of the coil 512. The diameter D (or radius R) defines a curved portion 512 of the truncated circle shape of the perimeter. In the depicted embodiment, the curved portion 512 is called the primary arc portion and has a primary arc length $S_1$. The truncated circle 501 is also defined by a substantially straight portion 514 or a chord. The substantially straight portion 514 can connect to the curved portion 512 at a curved or sharp interface 520, although a curved interface can be more desirable to reduce or prevent damage, stress, or kinks to the coil 512. In the depicted embodiment, the chord 514 is a distance $R_T$ from a line parallel to the substantially straight portion 514 that also intersects the center C of the truncated circle 501. The substantially straight portion 514 has a chord length $C_L$. The truncated circle 501 can also be defined by the absent circular segment 516 partially defined by the substantially straight portion 514 and a secondary arc portion length $S_2$. A center point of the secondary arc portion 518 is a distance $R_S$ from the substantially straight portion 514. The radius of the curved portion 512 of the truncated circle can be defined as Equation II:

$$R = R_T + R_S$$

In certain embodiments, the primary arc portion length $S_1$ can be about 70% to about 90% of the total length of the perimeter, which is the sum of the primary arc portion length $S_1$ and the chord length $C_L$. In other embodiments, the primary arc portion length $S_1$ is about 75% of the total length of the perimeter. The truncated circle and the circular segment 516 define areas bound by, respectively, the primary arc portion 512 and chord 514, and the secondary arc portion 518 and chord 514. In embodiments, the area of the circular segment 516 can be between about 5% and about 25% of the area of a complete circle (which includes the area of the truncated circle 501 and the circular segment 516). In other embodiments, the area of the circular segment 516 is about 10% of the area of the complete circle.

Figure 7:
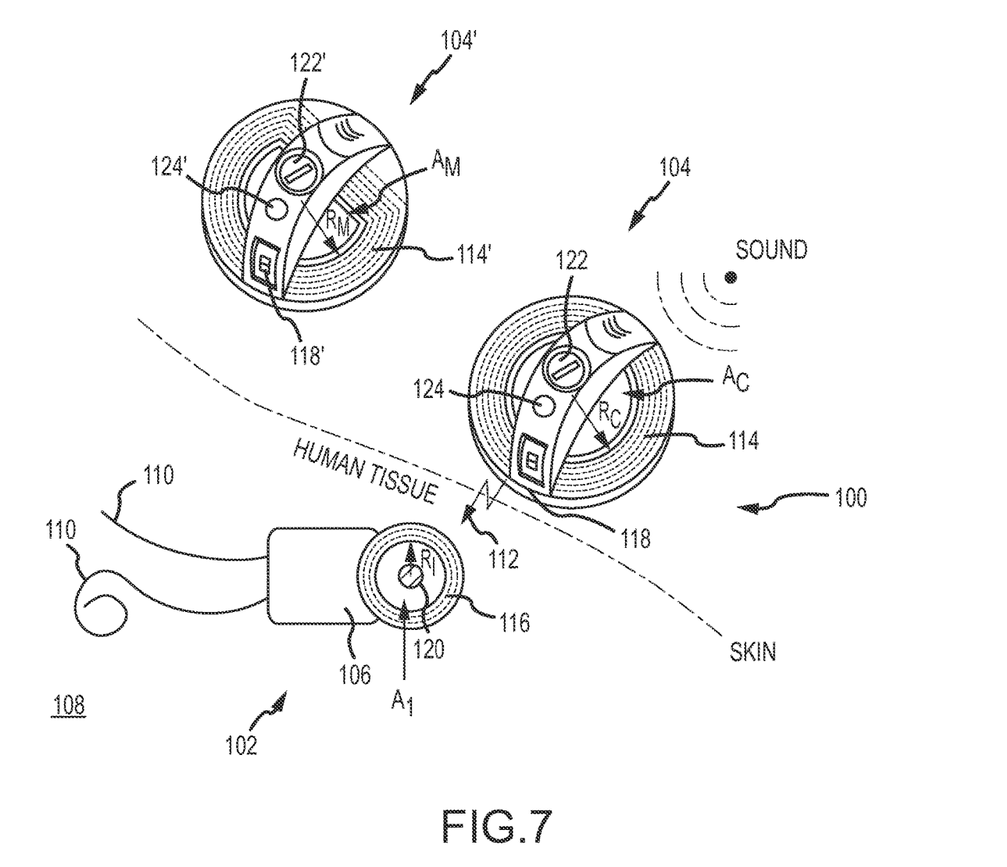
FIG. 7 depicts an auditory prosthesis, including an implantable coil portion, an external control coil portion, and an external modified coil portion in accordance with an embodiment of the present disclosure.

FIG. 7 depicts an auditory prosthesis 100, including an implantable portion 102, an external control portion 104, and an external modified portion 104' in accordance with an embodiment of the present disclosure. The various elements depicted are described generally in FIG. 1, and thus generally are not described further. The implantable portion 102 includes an implantable coil 116 that, in this embodiment, has a generally circular base form factor. The implantable coil 116 has a radius $R_I$ and an area $A_I$ defined by the radius $R_I$. The external control portion 104 includes an external control coil 114. That also has a generally circular form factor. The external control coil 114 has a radius $R_C$ and an area $A_C$ defined by the radius $R_I$. In certain embodiments, $R_C$ can be greater than $R_I$ to help ensure adequate data transmission from the external control coil 114 to the implantable coil 116. FIG. 7 also depicts an external modified portion 104', which is an external portion of the auditory prosthesis 100. The external modified portion 104' includes the same components as the external control portion 104, e.g., a magnet 122', an indicator 118', and so on. The coil 114', however is a modified coil, in that it has a modified base form factor substantially similar to the base form factor of the implantable coil 116, and that has a radius $R_M$ and an area $A_M$ defined at least in part by the radius $R_M$. The substantial similarity stems from the condition that the implantable coil 116 has a circular base form factor, while the modified base form factor of the modified external coil 114' is a truncated circle. In certain embodiments, the radius $R_M$ of the modified external coil 114' is larger than the radius $R_C$ of the control coil 114. However, due to the truncated circle shape of the modified external coil 114', the area $A_M$ of the modified external coil 114' is less than the area $A_C$ of the external control coil 114. In other embodiments, the radius $R_C$ of the external control coil 114 is substantially the same as the radius $R_M$ of the modified external coil 114'.

Figure 8:
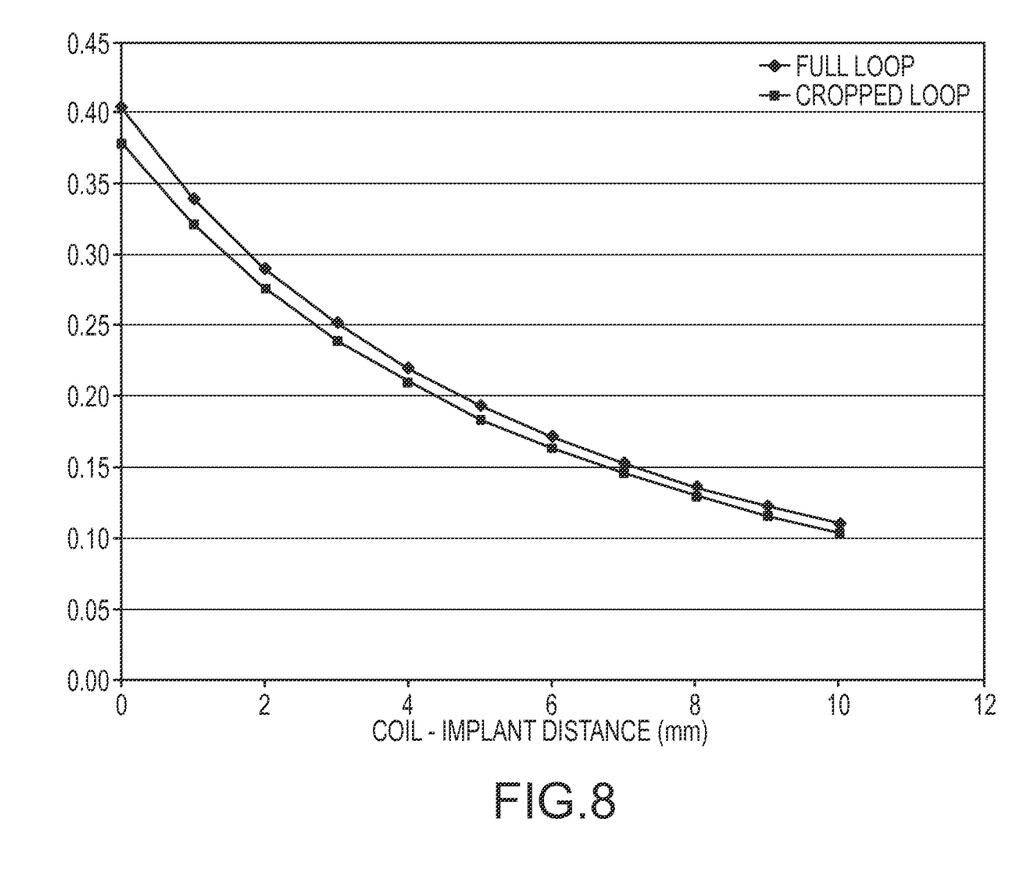
FIG. 8 depicts a comparison plot of coil coupling between coils having different form factors.

FIG. 8 depicts a comparison plot of coil coupling coefficient k between coils having different form factors. For the auditory prosthesis depicted in FIG. 7 above, where an implantable coil is utilized with an external control coil or a modified external coil, the coil coupling coefficient k can be measured between the implanted coil and either external coil (i.e., the control coil or the modified coil). As can be seen from the plot, the coil coupling coefficient k between an implanted coil and a truncated circle coil is between about 92% to about 96% of the coil coupling coefficient k between an implanted coil and a full coil, at various implant distances.

Figure 9:
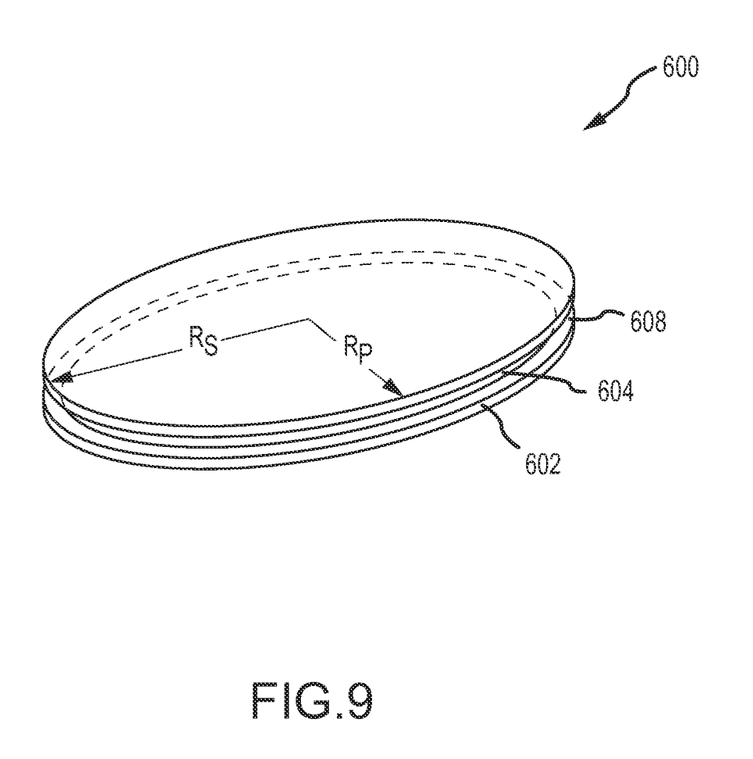
FIG. 9 depicts a top view of another bobbin utilized in embodiments of the present disclosure.

FIG. 9 depicts a top view of another bobbin 600 utilized in embodiments of the present disclosure. As with the embodiment of FIG. 7, the bobbin 600 includes a base plate 602 with a ring 604 extending therefrom. A second plate (not shown in this view) is disposed parallel to the base plate 602 so as to form a channel 608. The bobbin 600 is substantially oval in shape, and thus may be defined by a primary radius $R_P$ and a secondary radius $R_S$. It has been discovered that bobbins (and thus coils) having a form factor such as an oval can also be utilized with an implanted coil having a circular form factor while still maintaining acceptable coil quality Q and coil coupling k. Additionally, the non-round coils described herein need not be formed by wrapping a wire about a bobbin. For example, a non-round coil may be formed by traces on a printed circuit board.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. A system comprising:
   an implantable component comprising an implantable coil having a base form factor; and
   an external component comprising:
   a housing;
   an external coil defining an external coil perimeter and having a modified base form factor, wherein the modified base form factor is substantially similar to the base form factor, wherein the external coil is configured to transmit signals to the implantable coil, when the implantable coil is implanted in a recipient, and wherein the modified base form factor comprises a lateral perimeter portion defined in part by a substantially straight line; and
   a battery disposed laterally and entirely outside of the external coil perimeter and proximate a portion of the lateral perimeter portion defined by the substantially straight line,
   wherein the battery and the external coil are disposed within the housing.

2. The system of claim 1, wherein the base form factor comprises a circular shape.

3. The system of claim 2, wherein the modified base form factor comprises at least one of a D-shape and a truncated circle shape.

4. The system of claim 1, wherein the base form factor comprises a coil perimeter having a perimeter portion defined by a single first radius.

5. The system of claim 1, wherein the external component further comprises a module, wherein the module is disposed within the housing.

6. The system of claim 1, wherein the substantially straight line comprises a plurality of substantially straight lines.

7. The system of claim 1, wherein the external coil comprises a first radius and a first area and the implantable coil comprises a second radius that is equal to or smaller than the first radius and a second area that is greater than the first area.

8. The system of claim 1, wherein the base form factor comprises a first circumference and the modified form factor comprise a second circumference, wherein the first circumference is substantially the same as the second circumference.

9. The system of claim 1, wherein the base form factor is a circle with a first radius and a portion of the modified form factor is circular, the circular portion of the modified form factor has a second radius, and the second radius is substantially equal to the first radius.

10. The system of claim 1, wherein the external coil is formed from a plurality of substantially concentric loops.

11. An apparatus comprising:
    a wearable housing having a housing perimeter;
    an external coil comprising a lateral perimeter defined by a truncated circle comprising a primary arc portion and a substantially straight line portion, the external coil having an external coil shape and disposed within the housing perimeter;
    a battery disposed between the housing perimeter and entirely outside of the lateral perimeter of the external coil at a location proximate the substantially straight line portion; and
    an implantable coil having an implantable coil shape that is substantially similar to the external coil shape,
    wherein the external coil is configured to transmit a signal to the implantable coil when the implantable coil is implanted in a recipient.

12. The apparatus of claim 11, wherein the primary arc portion comprises a primary arc length between about 70% and about 90% of a length of the lateral perimeter.

13. The apparatus of claim 12, wherein the primary arc portion comprises a primary arc length about 75% of the length of the lateral perimeter.

14. The apparatus of claim 11, wherein an area of the truncated circle is defined by a circular area defined by a radius minus a circular segment area defined at least in part by the radius and a chord.

15. The apparatus of claim 14, wherein the circular segment area is about 25% to about 5% of the circular area.

16. The apparatus of claim 15, wherein the circular segment area is about 10% of the circular area.

17. The apparatus of claim 11, wherein the apparatus comprises an external portion of an auditory prosthesis, wherein the auditory prosthesis comprises the battery.

18. The apparatus of claim 11, wherein the external coil is formed from a plurality of substantially concentric loops.

19. The apparatus of claim 11, wherein the apparatus is a medical device, wherein the external coil is disposed within the housing adjacent the housing perimeter for at least 70% of the length of the housing perimeter.

20. The apparatus of claim 19, wherein the external coil diverges from the housing perimeter for at least 10% of the length of the housing perimeter.

21. The apparatus of claim 19, wherein the external coil is disposed adjacent a skin facing surface of the device, and wherein the skin facing surface defines the perimeter of the housing.

* * * * *